United States Patent [19]

Quinlan

[11] Patent Number: 4,578,243
[45] Date of Patent: Mar. 25, 1986

[54] INHIBITING CORROSION WITH QUATERNARY AMMONIUM DERIVATIVES OF 1,4-THIAZINE SULFONIC ACIDS

[75] Inventor: Patrick M. Quinlan, Webster Groves, Mo.

[73] Assignee: Petrolite Corporation, St. Louis, Mo.

[21] Appl. No.: 737,959

[22] Filed: May 28, 1985

Related U.S. Application Data

[62] Division of Ser. No. 226,300, Jan. 19, 1981.

[51] Int. Cl.$^4$ .......................... C23F 11/00; C23F 11/04
[52] U.S. Cl. ..................................... 422/7; 252/8.55 E; 252/391; 422/12; 422/16
[58] Field of Search .......................... 252/8.55 E, 391; 422/12, 16, 7

[56] References Cited

U.S. PATENT DOCUMENTS

| | | | |
|---|---|---|---|
| 4,188,359 | 2/1980 | Quinlan | 252/391 X |
| 4,217,329 | 8/1980 | Quinlan | 252/391 X |
| 4,312,830 | 1/1982 | Quinlan | 252/391 X |
| 4,312,831 | 1/1982 | Quinlan | 252/391 X |

Primary Examiner—Richard D. Lovering
Attorney, Agent, or Firm—Robert E. Wexler

[57] ABSTRACT

This invention relates to compositions of the formula

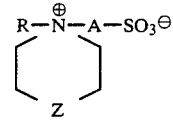

where R is a hydrocarbon, A is alkylene, and Z is S, SO, $SO_2$, and salts thereof. This invention also relates to uses thereof, for example as microbiocidal agents, corrosion inhibitors, etc.

2 Claims, No Drawings

INHIBITING CORROSION WITH QUATERNARY AMMONIUM DERIVATIVES OF 1,4-THIAZINE SULFONIC ACIDS

This is a division, of application Ser. No. 226,300, filed Jan. 19, 1981 pending.

This invention pertains to compounds having the following general formulas

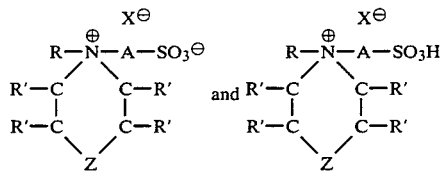

where the R"s are hydrogen or a substituted group such as a hydrocarbon group, i.e., alkyl, etc.; R is a hydrocarbon group such as alkyl, cycloalkyl, aralkyl, or a substituted alkyl such as hydroxyalkyl and the like; Z is S, SO, $SO_2$, A is alkylene, and X is an anion.

The compounds of this invention are prepared by the following sequence of reactions. The general example is:

(1)

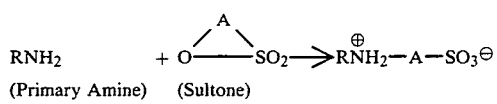

(Primary Amine) (Sultone)

A specific example is

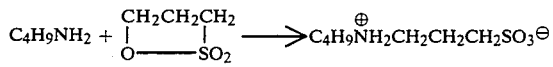

The reaction of primary amines with sultones has been known for some time and the preparation of the sulfobetaines has been described by C. Allen, et. al in The Journal of Analytical Chemistry, 37, No. 1, 156(1965) and by N. Parris, et. al. in The Journal of the American Oil Chemist Society, 50, 509 (1973).

(2) I have found that the sulfobetaines can be further reacted with a divinyl sulfur compound to give the 1,4-tetrahydrothiazine zwitterion. The general example is:

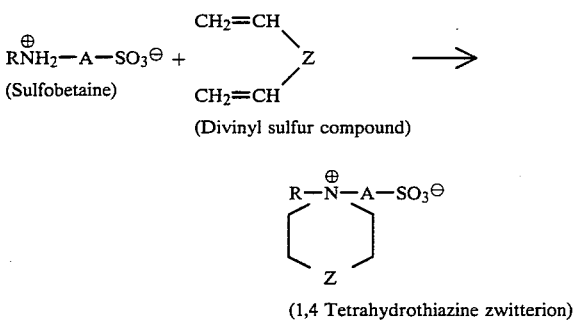

(1,4 Tetrahydrothiazine zwitterion)

A specific example is:

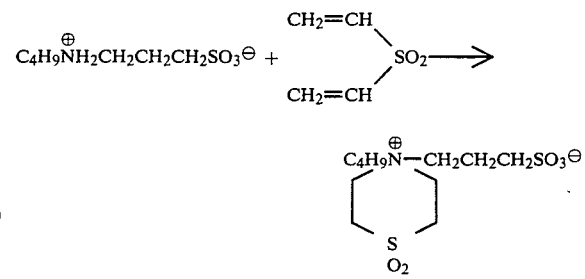

The reaction of a divinyl sulfur compound with primary and secondary amines to form the tetrahydrothiazine 1:1 dioxides is described in U.S. Pat. Nos. 3,828,036 and 4,113,709. These patents are included as if part hereof. The reaction of divinyl sulfone with a number of amino-acids is described by A. H. Ford-Moore, J. Chem. Soc. (1949), 2433.

(3) The final reaction concerns the formation of the salt of the compounds of reaction (2) by the addition of the appropriate acid to the sulfobetaine. The general reaction is:

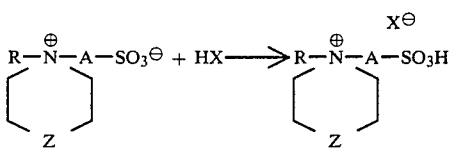

A specific example is:

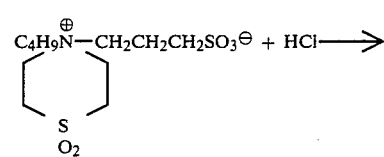

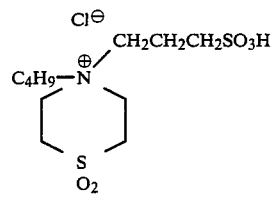

Suitable acids that may be employed to form the salts include inorganic and organic acid such as by way of example, hydrochloric, hydrobromic, hydroiodic, etc.; sulfuric, phosphonic, nitric, perchloric, methanesulfonic, xylenesulfonic, and the like.

Sultones useful in the preparation of the sulfobetaines include propane, 2,4-butane and 1,1,3-trimethyl propane. Primary amines suitable for reaction with the sultones include ethyl, n-propyl, n-pentyl, n-hexyl, n-octyl, n-decyl, n-dodecyl, n-tetradecyl, isobutyl, sec-butyl, cyclohexyl, t-butyl, t-octyl, benzyl, ethanolamine, and the like.

Examples of divinyl sulfur compounds useful in this invention include $CH_2=CHSCH=CH_2$ $CH_2=CHSOCH=CH_2$ $CH_2=CHSO_2CH=CH_2$ The preparation of the compounds of this invention may be illustrated by the following examples.

EXAMPLE 1

9.8 g. (0.05 mol) of $C_4H_9^{\oplus}NH_2CH_2CH_2CH_2SO_3^{\ominus}$ was warmed to 50° C. with 5.9 g. (0.05 mol) of divinyl sulfone in 25 ml. of a 50:50 mixture of ethanol and water. After heating for 3 hours, the reaction mixture was cooled and the solid reaction product was filtered off and washed several times with cold aqueous ethanol. The product was air dried. It was crystallized from absolute ethanol.

EXAMPLE 2

The chloride formed fine crystals from dilute ethanol containing a little hydrochloric acid. (Found: $Cl^{\ominus}$, 11.11%. $C_{11}H_{24}O_5NClS$ required $Cl^{\ominus}$, 11.18%)

The product had the following structure as confirmed by its IR, and NMR spectra.

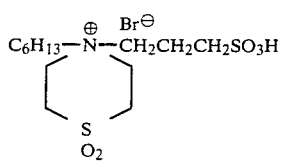

EXAMPLE 3

11.3 g. (0.05 mol) of $C_6H_{13}^{\oplus}NH_2CH_2CH_2CH_2SO_3^{\ominus}$ was warmed for 4 hrs. with 5.9 g. (0.05 mol) of divinyl sulfone in 25 ml. of aqueous ethanol. The isolated solid was filtered, washed with cold aqueous ethanol and dried.

EXAMPLE 4

The bromide formed fine needles from dilute ethanol containing a little hydrobromic acid (Found: $Br^{\ominus}$, 20.41%) $C_{13}H_{28}O_5NBrS$ required $Br^{\ominus}$, 20.51%.

The product had the following structure:

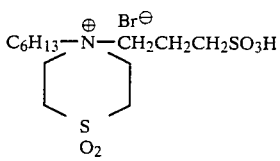

EXAMPLE 5

12.6 g. (0.05 mol) of $C_8H_{17}^{\oplus}NH_2CH_2CH_2CH_2SO_3^{\ominus}$ was warmed for 4 hrs. with 5.9 g. (0.05 mol) of divinyl sulfone in 25 ml. of absolute ethanol. Upon cooling the product crystallized from solution. The isolated solid was filtered, washed several times with cold ethanol and dried.

EXAMPLE 6

The iodide formed fine needles from aqueous ethanol containing a little hydroiodic acid. (Found: $I^{\ominus}$, 27.11%) $C_{15}H_{32}O_5NIS$ required $I^{\ominus}$, 27.31%.

The product had the following structure:

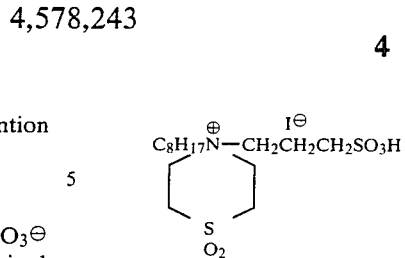

EXAMPLE 7

14.7 g. (0.05 mol) of $C_{12}H_{25}^{\oplus}NH_2CH_2CH_2CH_2SO_3^{\ominus}$ was warmed with 5.9 g. (0.05 mol) of divinyl sulfone in 30 ml. of ethanol. The reaction time was 4 hours. The product separated upon cooling.

EXAMPLE 8

The purified product was reacted with hydrochloric acid in aqueous ethanol to form the chloride. (Found: $Cl^{\ominus}$, 8.26%)

The product had the following structure:

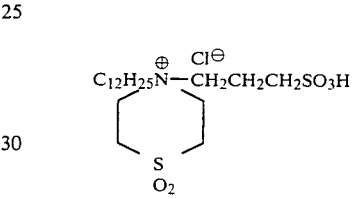

EXAMPLE 9

17.1 g. (0.05 mol) of $C_{14}H_{29}^{\oplus}NH_2CH_2CH_2CH_2SO_3^{\ominus}$ was warmed with 5.9 g. (0.05 mol) of divinyl sulfone in 35 ml. of ethanol. After reacting for 4 hours, the product was filtered, washed several times with cold ethanol and air dried.

EXAMPLE 10

The purified product was reacted with hydrochloric acid in ethanol to form the chloride salt.

The product had the following structure:

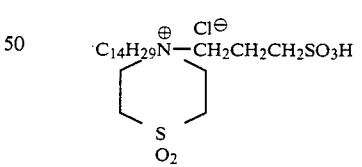

EXAMPLE 11

14.0 g. (0.05 mol) of $C_{10}H_{21}^{\oplus}NH_2CH_2CH_2CH_2SO_3^{\ominus}$ was warmed with 5.9 g (0.05 mol) of divinyl sulfone in 30 ml. of ethanol. The isolated product was purified as before.

EXAMPLE 12

The purified product was reacted with hydrochloric acid in ethanol to form the chloride salt. The salt had the following structure:

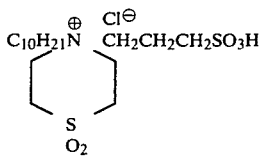

To avoid repetitive detail, the following table was constructed to illustrate further examples of this invention.

TABLE I $$R\overset{\oplus}{-}N-A-SO_3H \quad X^{\ominus}$$
(with SO$_2$ ring)

| Ex. | R | A | X |
|---|---|---|---|
| 13 | n-C$_3$H$_7$ | C$_4$H$_8$ | Br |
| 14 | n-C$_7$H$_{15}$ | C$_3$H$_6$ | NO$_3$ |
| 15 | i-C$_4$H$_9$ | C$_4$H$_8$ | CH$_3$COO |
| 16 | t-C$_4$H$_9$ | C$_3$H$_6$ | Br |
| 17 | cyclohexyl | C$_3$H$_6$ | Cl |
| 18 | benzyl (PhCH$_2$) | C$_3$H$_6$ | I |
| 19 | C$_{18}$H$_{37}$ | C$_3$H$_6$ | Cl |
| 20 | n-C$_4$H$_9$ | C$_4$H$_8$ | Br |
| 21 | sec-C$_4$H$_9$ | C$_6$H$_{12}$ | I |

The products of this invention are useful as corrosion inhibitors, microbiocides and surfactants.

USE AS A MICROBIOCIDE

(I) In water treatment

This phase of the present invention relates to the treatment of water. More particularly, it is directed to providing improved means for controlling microbiological organisms including bacteria, fungi, algae, protozoa, and the like, present in water.

It is well known that ordinary water contains various bacteria, fungi, algae, protozoa and other microbiological organisms which, if uncontrolled, multiply under certain conditions so as to present many serious problems. For example, in swimming pools the growth of these microbiological organisms is very undesirable from a sanitary standpoint as well as for general appearances and maintenance. In industrial water systems such as cooling towers, condenser boxes, spray condensers, water tanks, basins, gravel water filters, and the like, microbiological organisms may interfere greatly with proper functioning of equipment and result in poor heat transfer, clogging of systems and rotting of wooden equipment, as well as many other costly and deleterious effects.

In other industrial applications where water is used in processes, as for example, as a carrying medium, etc., microbiological organisms may also constitute a problem in maintenance and operation. Illustrative of such industrial applications are the pulp and paper manufacturing processes, oil well flooding operations and the like.

The products of this invention are suitable as biocides for industrial, agricultural and horticultural, military, hygienic and recreational water supplies. They provide an inexpensive, easily prepared group of products which can be used, in minimal amounts, in water supplies, in cooling towers, air-conditioning systems, on the farm and ranch, in the factory, in civilian and military hospitals and dispensaries, in camps, for swimming pools, baths and aquaria, waterworks, wells, reservoirs, by fire-fighting agencies, or maritime and naval vessels, in boilers, steam-generators and locomotives, in pulp and paper mills, for irrigation and drainage, for sewage and waste disposal, in the textile industry, in the chemical industries, in the tanning industry, et cetera, and which will render said water supplies bactericidal, fungicidal and algicidal. They further provide a simple process whereby water supplies, for whatever purposes intended, are rendered bacteriostatic, fungistatic and algistatic, i.e., said water supplies treated by the process of this invention will resist and inhibit the further growth or proliferation of bacteria, fungi, algae and all forms of microbial life therein.

(II) Water flooding in secondary recovery of oil

This phase of the present invention relates to secondary recovery of oil by water flooding operations and is more particularly concerned with an improved process for treating flood water and oil recovery therewith. More particularly this invention relates to a process of inhibiting bacterial growth in the recovery of oil from oil-bearing strata by means of water flooding taking place in the presence of sulfate-reducing bacteria.

Water flooding is widely used in the petroleum industry to effect secondary recovery of oil. By employing this process the yield of oil from a given field may be increased beyond the 20-30 percent of the oil in a producing formation that is usually recovered in the primary process. In flooding operation, water is forced under pressure through injection wells into or under oil-bearing formations to displace the oil therefrom to adjacent producing wells. The oil-water mixture is usually pumped from the producing wells into a receiving tank where the water, separated from the oil, is siphoned off, and the oil then transferred to storage tanks. It is desirble in carrying out this process to maintain a high rate of water injection with a minimum expenditure of energy. Any impediment to the free entry of water into oil-bearing formations seriously reduces the efficiency of the recovery operation.

The term "flood water" is herein employed is any water injected into oil-bearing formations for the secondary recovery of oil. In conventional operations, the water employed varies from relatively pure spring water to brine and is inclusive of water reclaimed from secondary recovery operations and processed for recycling. The problems arising from the water employed depend in part on the water used. However, particularly troublesome and common to all types of water are problems directly or indirectly concerned with the presence of microorganisms, such as bacteria, fungi and algae. Microorganisms may impede the free entry of water into oil-bearing formations by producing ions susceptible of forming precipitates, forming slime and/or existing in sufficiently high numbers to constitute an appreciable mass, thereby plugging the pores of the oil-bearing formation. Free-plugging increases the pressure necessary to drive a given colume of water into an oil-bearing formation and oftentimes causes the flooding water to by-pass the formation to be flooded. In addition, microorganisms may bring about corrosion by acting on the metal structures of the wells involved, producing corrosive substances such as hydrogen sulfide, or producing conditions favorable to destructive corrosion such as decreasing the pH or producing oxygen. The products formed as the result of corrosive action may also be pore-plugging precipitates. Usually, the difficulties encountered are a combination of effects resulting from the activity of different microorganisms.

(III) Hydrocarbon treatment

This phase of the present invention relates to the use of these compounds as biocides in hydrocarbon systems.

In addition to being used as biocides in aqueous systems, the compounds of this invention can also be employed as biocides in hydrocarbon systems, particularly when petroleum products are stored. It is believed that bacteria and other organisms, which are introduced into hydrocarbon systems by water, feed readily on hydrocarbons resulting in a loss in product; that microorganisms cause the formation of gums, $H_2S$, peroxides, acids and slimes at the interface between water and oil; that bacterial action is often more pronounced with rolling motion than under static conditions, etc. Loss of product, corrosion of the storage tank, clogging of filters and metering instruments, and fuel deterioration are among the harmful effects of bacteria growth in fuels. The activity of microorganism growth is often increased by the presence of rust. Not only do these microorganisms often encourage rust but rust encourages microorganism growth. Since microorganism growth appears to be considerably higher with kerosene than with gasoline, plugged filters experienced with jet fuels which contain large amounts of kerosene is a serious problem.

The compositions of this invention can be employed in hydrocarbon systems.

MICROBIOCIDAL TESTING

The screening procedure was as follows: a one percent by weight solution of the test compound in water was prepared. The solution was aseptically added to a sterile broth that would support the growth of the test organism, *Desulfovibro desulfuricans*, to provide a concentration of 50 and 100 parts by weight of test compound per million parts by weight of broth. A general growth medium, such as prescribed by the American Petroleum Institute was used. The broth containing the test compound then was dispersed in 5 cc. amounts into sterile disposable tubes and the tubes were inoculated with the growing test organism and incubated at 35° C. for 24 hours. The absence or presence of growth of the microorganisms was determined by visual inspection by an experienced observer.

Following is a summary of the results of the testing of examples of this invention.

| Compound example no. | Concentration of test compound, p.p.m. | Results |
| --- | --- | --- |
| 7 | 25 | Gave control[1] |
| 8 | 25 | Gave control[1] |
| 9 | 25 | Gave control[1] |
| 10 | 25 | Gave control[1] |
| 11 | 50 | Gave control[1] |
| 12 | 50 | Gave control[1] |

[1] By control is meant that the test compound was biostatic or biocidal - i.e., no growth of the test-organism occurred under the test conditions.

USE IN BRINES

This phase of the invention relates to the prevention of corrosion in systems containing a corrosive aqueous medium, and most particularly in systems containing brines.

More particularly, this invention relates to the prevention of corrosion in the secondary recovery of petroleum by water flooding and in the disposal of waste water and brine from oil and gas wells. Still more particularly, this invention relates to a process of preventing corrosion in water flooding and in the disposal of waste water and brine from oil and gas wells which is characterized by injecting into an underground formation an aqueous solution containing minor amounts of compositions of this invention, in sufficient amounts to prevent the corrosion of metals employed in such operation. This invention also relates to corrosion inhibited brine solutions of these compounds.

When an oil well ceases to flow by the natural pressure in the formation and/or substantial quantities of oil can no longer be obtained by the usual pumping methods, various processes are sometimes used for the treatment of the oil-bearing formation in order to increase the flow of the oil. These processes are usually described as secondary recovery processes. One such process which is used quite frequently is the water flooding process wherein water is pumped under pressure into what is called an "injection well" and oil, along with quantities of water, that have been displaced from the formation, are pumped out of an adjacent well usually referred to as a "producing well." The oil which is pumped from the producing well is then separated from the water that has been pumped from the producing well and the water is pumped to a storage reservoir from which it can again be pumped into the injection well. Supplementary water from other sources may also be used in conjunction with the produced water. When the storage reservoir is open to the atmosphere and the oil is subject to aeration this type of water flooding system is referred to herein as an "open water flooding system."

Because of the corrosive nature of oil field brines, to economically produce oil by water flooding, it is necessary to prevent or reduce corrosion since corrosion increases the cost thereof by making it necessary to repair and replace such equipment at frequency intervals.

I have now discovered a method of preventing corrosion in systems containing a corrosive aqueous media, and most particularly in systems containing brines, which is characterized by employing the compositions of this invention.

I have also discovered an improved process of protecting from corrosion metallic equipment employed in secondary oil recovery by water flooding such as injection wells, transmission lines, filters, meters, storage tanks, and other metallic implements employed therein and particularly those containing iron, steel, and ferrous alloys, such process being characterized by employing in water flood operation the compositions of this invention.

This phase of the invention then is particularly concerned with preventing corrosion in a water flooding process characterized by the flooding medium containing an aqueous or an oil field brine solution of these compounds.

In many oil fields large volumes of water are produced and must be disposed of where water flooding operations are not in use or where water flooding operations cannot handle the amount of produced water. Most states have laws restricting pollution of streams and land with produced waters, and oil producers must then find some method of disposing of the waste produced salt water. In many instances, therefore, the salt water is disposed of by injecting the water into permeable low pressure strata below the fresh water level. The formation into which the water is injected is not the oil producing formation and this type of disposal is defined as salt water disposal or waste water disposal. The problems of corrosion of equipment are analogous to those encountered in the secondary recovery operation by water flooding.

The compositions of this invention can also be used in such water disposal wells thus providing a simple and economical method of solving the corrosion problems encountered in disposing of unwanted water.

Water flood and waste disposal operations are too well known to require further elaboration. In essence, in the present process, the flooding operation is effected in the conventional manner except that the flooding medium contains a minor amount of the compound of this invention, sufficient to prevent corrosion, in concentrations of about 10 p.p.m. to 10,000 p.p.m., or more, for example, about 50 to 5,000 p.p.m., but preferably about 15 to 1,500 p.p.m. The upper limiting amount of the compounds is determined by economic considerations. Since the success of a water flooding operation manifestly depends upon its total cost being less than the value of the additional oil recovered from the oil reservoir, it is quite important to use as little as possible of these compounds consistent with optimum corrosion inhibition. Optimum performance is generally obtained employing about 5-100 p.p.m. Since these compounds are themselves inexpensive and are used in low concentrations, they enhance the success of a flood operation by lowering the cost thereof.

While the flooding medium employed in accordance with the present invention contains water or oil field brine and the compounds, the medium may also contain other materials. For example, the flooding medium may also contain other agents such as surface active agents or detergents which aid in wetting throughout the system and also promote the desorption of residual oil from the formation, sequestering agents which prevent the deposition of calcium and/or magnesium compounds in the interstices of the formation, bactericides which prevent the formation from becoming plugged through bacterial growth, tracers, etc. Similarly, they may be employed in conjunction with any of the operating techniques commonly employed in water flooding and water disposal processes, for example five spot flooding, peripheral flooding, etc., and in conjunction with other secondary recovery methods.

The following examples illustrate the use of the compositions of this invention as corrosion inhibitors.
Conditions:
2% NaCl Solution
Atm. Pressure
Room Temperature
Constant $CO_2$ sparge (Coleman Instrument Grade)
Constant stirring
500 p.p.m. of inhibitor based on active component

| Example Number | Corrosion Rate (mpy) 1 Hr. | 24 Hrs. | % Protection |
|---|---|---|---|
| 5 | 65 | 30 | 83 |
| 6 | 55 | 25 | 81 |
| 7 | 8 | 7 | 94 |
| 8 | 6 | 5 | 96 |
| 9 | 12 | 8 | 94 |
| 10 | 9 | 7 | 94 |
| 11 | 25 | 20 | 86 |
| 12 | 20 | 16 | 90 |
| 19 | 16 | 12 | 92 |
| Blank | 135 | 165 | — |

I claim:

1. A process of treating a metallic surface in contact with a corrosive environment comprising adding to said environment a corrosion inhibiting amount of a composition having the formula

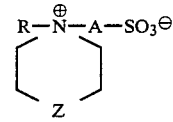

when R is selected from the group consisting of alkyl, cycloalkyl, aralkyl and hydroxyalkyl, A is alkylene, Z is S, SO or $SO_2$.

2. A process of treating a metallic surface in contact with a corrosive environment comprising adding to said environment a corrosion inhibiting amount of a composition having the formula

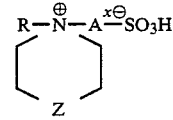

where R is selected from the group consisting of alkyl, cycloalkyl, aralkyl and hydroxyalkyl, A is alkylene, Z is S, SO or $SO_2$ and X is an anion.

* * * * *